United States Patent [19]
Day et al.

[11] Patent Number: 5,895,396
[45] Date of Patent: Apr. 20, 1999

[54] SURGICAL PINS

[75] Inventors: Ralph Paul Day, West Linton; Kenneth Robert Anderson, Gorebridge, both of United Kingdom

[73] Assignee: Ethicon, Inc., Somerville, N.J.

[21] Appl. No.: 08/663,494

[22] Filed: Jun. 14, 1996

[30] Foreign Application Priority Data

Jun. 15, 1995 [GB] United Kingdom ............... 9512128

[51] Int. Cl.$^6$ ........................................... A61B 17/04
[52] U.S. Cl. ........................................... 606/151; 606/72
[58] Field of Search ................................ 606/232, 72–75

[56] References Cited

U.S. PATENT DOCUMENTS

| | | | |
|---|---|---|---|
| 5,236,438 | 8/1993 | Wilk | 606/215 |
| 5,333,624 | 8/1994 | Tovey | 128/897 |
| 5,350,387 | 9/1994 | Semm | 606/151 |
| 5,492,452 | 2/1996 | Kirsch et al. | 411/455 |

FOREIGN PATENT DOCUMENTS

| | | | |
|---|---|---|---|
| 0 485 744 A1 | 5/1992 | European Pat. Off. | A61B 17/064 |
| 0 531 742 A1 | 3/1993 | European Pat. Off. | A61B 17/064 |
| 0 548 998 A1 | 6/1993 | European Pat. Off. | A61B 17/064 |
| 0 632 999 A1 | 1/1995 | European Pat. Off. | A61B 17/04 |
| 0 317 406 | 5/1989 | France | A61F 2/08 |
| WO 85/03857 | 9/1985 | WIPO | A61B 17/04 |
| WO 89/01767 | 3/1989 | WIPO | A61F 5/04 |
| WO 92/06638 | 4/1992 | WIPO | A61B 17/00 |

*Primary Examiner*—Gary Jackson
*Attorney, Agent, or Firm*—Hal Brent Woodrow

[57] ABSTRACT

A pin for attaching a surgical membrane barrier to tissue structure of a patient comprises a pin body 1 formed from a sequence of four truncated cones which define a serrated profile which enables the pin to engage the membrane barrier and to be pushed-fitted into the tissue structure. The head portion 2 of the pin serves to engage the membrane barrier and retain it in position on the underlying tissue structure.

The pin is made from a resorbable polymer, such as PDS Polydioxanone and is of substantially solid construction throughout.

In an alternative embodiment, a circularly cylindrical extension is provided between the largest truncated cone and the pin head. The arrangement serves to maintain a spacing between the membrane barrier and the underlying tissue.

24 Claims, 2 Drawing Sheets

SURGICAL PINS

THE FIELD OF THE INVENTION

The present invention relates to pins for attaching a surgical membrane barrier to tissue structure of a patient.

BACKGROUND OF THE INVENTION

It is known that, after performing certain surgical procedures on a patient, it can be desirable to place a membrane barrier on the site of the operation. Such membrane barriers exclude cell types such as epithelial elements, thereby promoting "productive" cell lines with the aim of encouraging qualitative and quantitative regeneration of functional tissue.

There are many clinical situations wherein a secondary means of fixing and retaining the appropriate membrane barrier to the underlying tissue structure is essential if the tissue regenerative process is to be encouraged.

It has long been recognised that secondary surgical interventions undertaken for the sole purpose of removing non-absorbable "scaffolding" structures (placed at the time of primary surgery) are undesirable. Apart from the additional discomfort and inconvenience to the patient, the secondary intervention can prejudice the quality and speed of the delicate biological regenerative process initiated soon after the placement of the membrane barrier.

The current systems available for providing membrane support are constructed from highly engineered medical grade titanium alloys. Apart from the disadvantages of requiring secondary surgery, as mentioned above, such titanium alloy systems are extremely expensive and require expensive manipulating instruments, such as drivers, graspers and surgical mallets. In addition, there is considerable difficulty with handling and manipulating such systems. Furthermore, the size constraints of existing designs can render it difficult to obtain adequate purchase in spongy cancellous bone.

It has therefore been considered desirable to provide a tissue tacking system made from a resorbable material, thereby precluding the need for secondary surgery, and to provide a system which overcomes the other disadvantages of conventional systems mentioned above.

Bone pins have therefore been made from synthetic resorbable polymers so as to overcome the need for secondary surgery. However, such bone pins have relied upon screw threading for retention, and this presents a major inherent problem in that they are unable to resist the high torque forces produced when attempting to fix them into dense bone.

It would therefore be desirable to provide a resorbable surgical pin which overcomes this disadvantage.

Pins made from synthetic resorbable polymers are known. These are of hollow construction to allow the pins to become infiltrated by, incorporated by, and ultimately resorbed by host tissue. However, this construction necessarily complicates the manufacturing process and is not feasible for pins having small dimensions. Furthermore, such a hollow construction is not necessary for facilitating the processes of guided tissue and/or bone regeneration.

SUMMARY OF THE INVENTION

In accordance with a first aspect of the present invention there is provided a pin for attaching a surgical membrane barrier to tissue structure of a patient, the pin being formed from a resorbable polymer and being of substantially solid construction throughout and having a profile which enables the pin to engage the membrane barrier and to be push-fitted into the tissue structure, in combination with a said surgical membrane barrier for use therewith.

In accordance with a second aspect of the present invention there is provided the use of a resorbable polymer to manufacture a pin therefrom for attaching a surgical membrane barrier to tissue structure of a patient, the pin being of substantially solid construction throughout and having a profile which enables the pin to engage the membrane barrier and to be push-fitted into the tissue structure.

The profile is advantageously provided by a serrated edge to the pin, such as provided by a sequence of truncated cones.

A suitable material for the resorbable pin is a polymer of p-dioxanone or poly[oxy(1-oxoethylene)oxyethylene], such as PDS Polydioxanone (R.T.M.), although a copolymer of glycolide with L (−) lactide, such as Vicryl Polyglactin 910 (R.T.M.) may alternatively be used. The chemical structures of these compounds are described in GB 1 540 053 and GB 1 416 196 respectively.

BRIEF DESCRIPTION OF THE DRAWINGS

Preferred embodiments of the present invention will now be described with reference to the accompanying drawings, wherein.

DETAILED DESCRIPTION OF THE INVENTION

Figure 1:
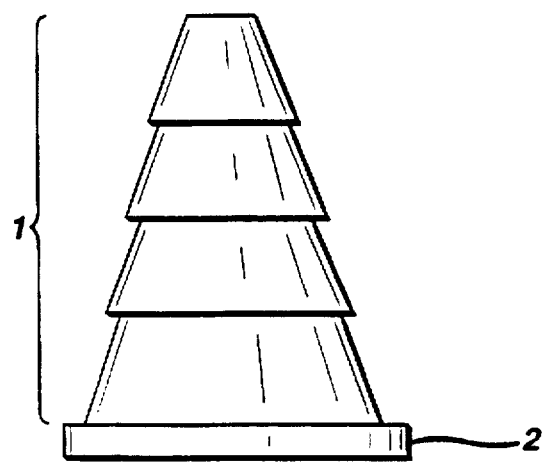
FIG. 1 shows an axial cross-section of a membrane pin in accordance with the present invention.

With reference to FIG. 1, the membrane barrier support pin comprises a pin body 1 of substantially solid construction throughout in the form of a sequence of truncated circular cones which are arranged so as to provide a serrated profile which can frictionally grip the sides of a pre-drilled hole in underlying body tissue, such as bone. The angle of each truncated cone is 70.6°. The minimum diameters of the truncated cones are respectively 0.5 mm, 0.7 mm, 0.9 mm and 1.1 mm, the maximum diameters being respectively 1.2 mm, 1.4 mm, 1.6 mm and 1.8 mm. The larger end of the pin body is provided with a circularly cylindrical head 2 having a diameter of 3.0 mm. This head serves to secure a resorbable membrane barrier in position on underlying body tissue.

Figure 2:
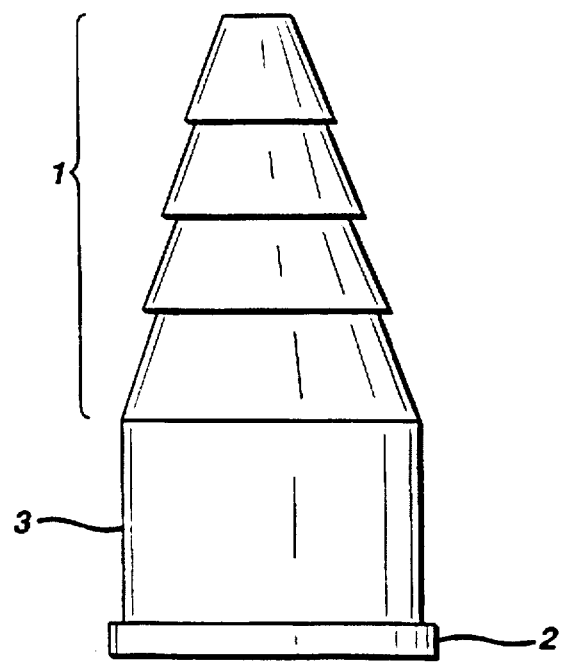
FIG. 2 shows an axial cross-section of a membrane pin incorporating a membrane support, also in accordance with the present invention.
Figure 3:
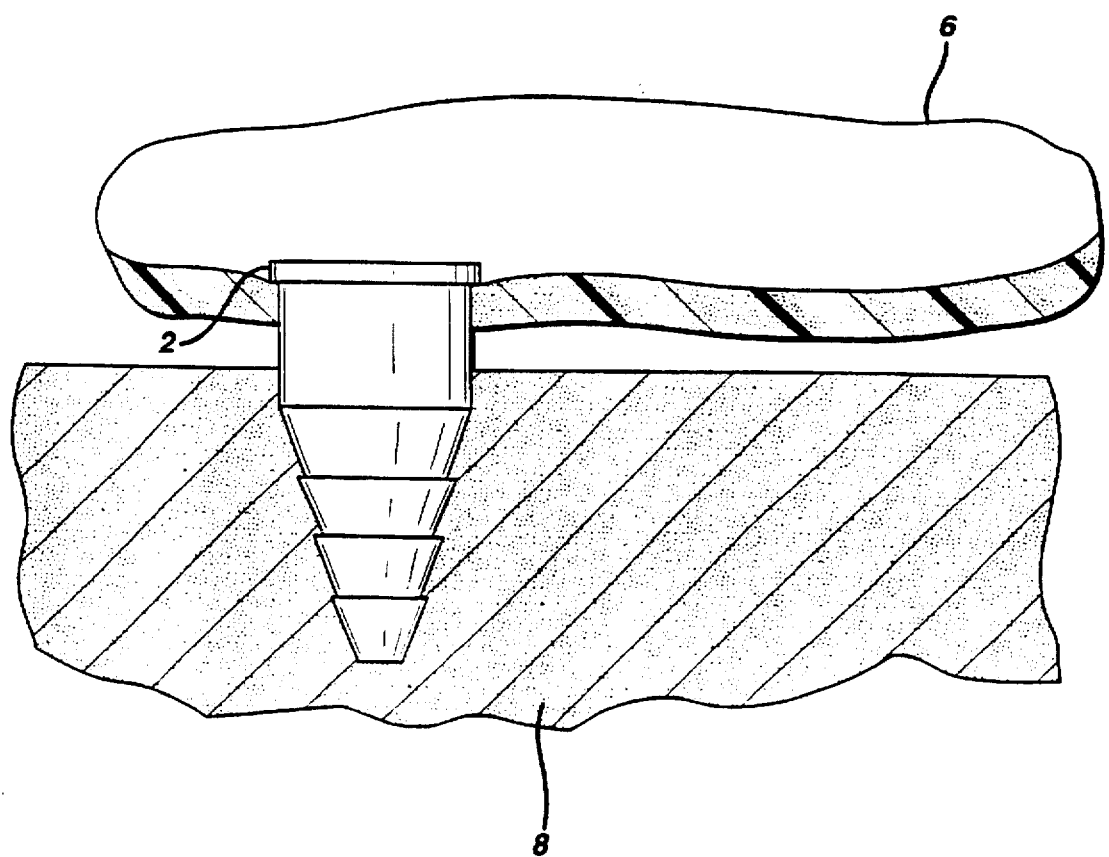
FIG. 3 shows a cross-section of the pin retaining a membrane.

An alternative embodiment is shown in FIG. 2, wherein, between the largest truncated cone and the head 2 there is provided circularly cylindrical extension having a length of 2 mm and a diameter of 1.8 mm. This serves to maintain an adequate spacing beneath the membrane barrier to allow consolidation and subsequent organisation of the blood clot, which is believed to be fundamental to the osteogenic process, since the osteocyte progenitor cells are contained therein. As with the embodiment shown in FIG. 1, the head 2 serves to retain the membrane barrier above the underlying body tissue.

In each case the pin is made from PDS Polydioxanone. This material advantageously provides residual intrinsic strength for up to six weeks after implantation.

The pins may be conveniently inserted by compaction into a pre-drilled 1 mm diameter channel in underlying tissue. Such channels are advantageously countersunk and made using a tungsten carbide tapered fissure bur running at low speed and continuously irrigated with sterile saline.

Pre-clinical, in-vivo experiments have additionally shown that membranes made from PDS Polydioxanone serve to promote osteogenesis, with the duality of the resultant bone being well-organised and vascularised, in marked contrast to the poorly-organised woven-type bone which has been observed following the use of resorbable barrier membranes of different construction and materials. It is therefore considered appropriate to manufacture the pin and the membrane barrier from the same polymeric material.

Membrane barrier pins in accordance with the present invention can conveniently be manufactured using compression or injection moulding techniques and can be conveniently manufactured in the form of a group of four such pins attached to a small removable stalk of PDS Polydioxanone to facilitate ease of handling by the clinician.

It will be appreciated that such membrane support pins have an extremely wide area of potential application, e.g:

1. Oral Surgery

Implantology: a membrane support for guided regeneration.

Periodontology: a membrane support for guided bone and tissue regeneration.

2. Maxillo-Facial/Cranio-Facial Surgery

Membrane Support to facilitate guided bone regeneration for bony defects, such as mandibular cyst cavities;
congenital defects, such as cleft palates;
maxillary sinus augmentation lifting;
orbital floor repairs (severe comminuted fractures).

3. Orthopaedic Surgery

Facilitation of guided bone or other tissue regeneration for many defects, both as a consequence of trauma surgery and elective surgery, e.g. non-union of fractures, such as of long bones; regeneration of large bony defects, such as in post-ablative surgery.

4. ENT Surgery

Membrane support to facilitate nasal septum reconstruction.

5. General/Plastic Surgery

Means for support of suture/tape slings used for tissue support, augmentation etc.

Although the present invention has been described with reference to preferred embodiments, it will be appreciated that numerous modifications and/or variations are contemplated by the present invention. For example, although specific dimensions of the membrane support pin have been given above, the size can of course be varied to satisfy the demands of the particular clinical application. In particular: the angle of each truncated cone could take any value within the range 67.5° to 750°; the profile could extend over any length between 2 mm and 10 mm; the spacer portion, if such is provided, could have any axial length within the range 2 mm to 5 mm; the minimum diameter of the pin could have any value between 0.5 mm and 2.0 mm; and the maximum diameter of the pin could have any value between 2 mm and 10 mm.

Although the membrane barrier pins of the present invention have been described in relation to the attaching of resorbable membrane barriers, it will be appreciated that advantages of the invention may still be gained even if a non-resorbable membrane barrier is attached using such pins. Furthermore, although the pins are preferably made from PDS Polydioxanone, it will be appreciated that any suitable resorbable polymer could be used, the choice of material being dependent on the strength retention profile required of the particular clinical application.

We claim:

1. A pin for attaching a surgical membrane barrier to a tissue structure of a patient, the pin being formed from a resorbable polymer and being of substantially solid construction throughout and having a profile which enables the pin to engage the membrane barrier wherein the profile is circumferentially continuous and to be push-fitted into the tissue structure, in combination with a said surgical membrane barrier for use therewith.

2. A pin as claimed in claim 1, wherein said surgical membrane barrier is formed from a resorbable polymer.

3. A pin as claimed in claim 1, wherein the profile is tapered.

4. A pin as claimed in claim 1, wherein the profile is serrated.

5. A pin as claimed in claim 1, wherein said sequence comprises four truncated cones.

6. A pin as claimed in claim 1, wherein the radial cross-section of said cones is substantially circular.

7. A pin as claimed in claim 1, wherein the angle of each cone is in the range 67.5 degrees to 75 degrees.

8. A pin as claimed in claim 7, wherein said angle is substantially 70.6 degrees.

9. A pin as claimed in claim 1, wherein the profile extends axially over a length of between 2 mm and 10 mm.

10. A pin as claimed in claim 9, wherein said length is substantially 4.0 mm.

11. A pin as claimed in claim 1, comprising a head and a spacer portion between said head and said profile.

12. A pin as claimed in claim 11, wherein said spacer portion has an axial length of between 2 mm and 5 mm.

13. A pin as claimed in claim 12, wherein said axial length of said spacer portion is substantially 2.0 mm.

14. A pin as claimed in claim 1, and having a substantially circular radial cross-section.

15. A pin as claimed in claim 14 and having a minimum diameter of between 0.5 mm and 2.0 mm.

16. A pin as claimed in claim 15, and having a minimum diameter of substantially 0.5 mm.

17. A pin as claimed in claim 14, and having a maximum diameter of between 2 mm and 10 mm.

18. A pin as claimed in claim 17 and having a maximum diameter of substantially 3.0 mm.

19. A pin as claimed in claim 1 and made from a polymer of p-dioxanone.

20. A pin as claimed in claim 19 and made from PDS Polydioxanone (R.T.M).

21. A pin as claimed in claim 1 and made from a polymer of poly[oxy(1-oxoethylene)oxyethylene].

22. A pin as claimed in claim 21 and made from PDS Polydioxanone (R.T.M).

23. A pin as claimed in claim 21 and made from Vicryl Polyglactin 910 (R.T.M.).

24. A pin as claimed in claim 1 and made from a copolymer of glycolide with L(−) lactide.

* * * * *